United States Patent [19]
Robinson

[11] Patent Number: 4,693,120
[45] Date of Patent: Sep. 15, 1987

[54] REAL TIME ULTRASONIC SCANNING METHOD AND APPARATUS

[75] Inventor: David E. Robinson, Bilgola Plateau, Australia

[73] Assignee: The Commonwealth of Australia, Australian Capital Territory, Australia

[21] Appl. No.: 877,485

[22] Filed: Jun. 23, 1986

[30] Foreign Application Priority Data

Jun. 26, 1985 [AU] Australia ............... PH1224

[51] Int. Cl.$^4$ ............................... G01N 29/04
[52] U.S. Cl. ....................... 73/618; 73/621; 73/633; 128/660
[58] Field of Search ................ 73/618, 621, 633, 641

[56] References Cited

U.S. PATENT DOCUMENTS

| | | | |
|---|---|---|---|
| 4,231,373 | 11/1980 | Waxman et al. | 73/621 |
| 4,233,988 | 11/1980 | Dick et al. | 73/633 |
| 4,252,025 | 2/1981 | Robinson | 128/660 |
| 4,418,698 | 12/1983 | Dory | 73/633 |

Primary Examiner—Anthony V. Ciarlante
Attorney, Agent, or Firm—Ladas & Parry

[57] ABSTRACT

A compound ultrasonic scan of an object is effected with a pair of transducers mounted adjacent to the object but spaced apart from each other. Each transducer is operated as a "wobbler" transducer. That is, the transducer transmits pulses of ultrasonic energy into the object and receives echoes from acoustic discontinuities in the object while the transducer is oscillated mechanically, through a predetermined angle, about an axis which passes through the transducer. The improvement of this invention is (i) the oscillation of the transducers is synchronism with each other but out of phase with each other, so that when one transducer is at the edge of its angular scan, the other transducer is at the center of its angular scan, and (ii) activating the transducers using a stream of electrical pulses which are supplied to the transducers so that when a transducer is at the center of its angular scan, it receives most of the activating pulses and when it is at the edge of its angular scan, it receives a small proportion of the activating pulses.

6 Claims, 5 Drawing Figures

MOTOR SHAFT ANGLE →
(OR TIME)

REAL TIME ULTRASONIC SCANNING METHOD AND APPARATUS

TECHNICAL FIELD

This invention concerns ultrasonic echoscopy. More particularly it concerns the preparation of echograms from compound scan imaging of an object. The invention is useful in medical imaging and in the non-destructive evaluation of objects into which ultrasonic energy can penetrate.

BACKGROUND TO THE INVENTION

The transmission of pulses of ultrasonic energy into an object and using the reflected echoes from acoustic discontinuities within the object to create a cross-sectional image of the object is a well-known technique in medical diagnosis and in non-destructive evaluation. In one application of this technique, called "compound scan imaging", the pulses of ultrasonic energy are directed into the object from a number of inspection positions and an intersecting pattern of lines of sight are established to provide a complete cross-sectional image of the object. Using compound scan imaging, a panoramic view of an entire cross-section of the object under investigation can be obtained. Areas are scanned from a number of directions, which provides good coverage of echoes from specularly reflecting surfaces and avoids problems due to local areas of shadowing, which would otherwise degrade areas of the image.

A disadvantage of the compound scan approach to ultrasonic imaging is that it usually requires a time period of several seconds to obtain an image. Any movement of the scanned object during this period causes distortion or blurring of the resultant image. Also, variation of the speed of sound in the various regions of the object tends to cause mis-mapping of echo position, and this, with overlapping scans, causes further image degradation.

In a relatively recent development in medical ultrasonic imaging, a single inspection point is used and a beam of ultrasonic energy is rapidly scanned to produce a sector of ultrasonic echo information in a fraction of a second. This process is repeated continuously and produces a continuously refreshed ultrasonic image which depicts the anatomy under investigation in cross-section. This technique is particularly useful for examining moving objects, such as the beating heart or the foetus, and is also useful for carrying out a rapid survey of the anatomy to establish which areas require closer examination.

The available frame rate (or rate of refreshment) of an ultrasound image is determined by the depth of penetration required, the speed of sound in the object (in human tissue this has an average value of 1540 meters per second), and the number of lines necessary to make a satisfactory image. For medical ultrasound imaging, the frame rate R is given by the relationship:

$$R = \frac{1540}{2Nd} \times 10^2$$

where N is the number of lines required and d is the required depth in cm.

The number of lines needed for a satisfactory image is set by the maximum angular distance between successive lines (which in turn is set by the beam width) and the total angle of the sector scan, provided the angular speed of scan generation is constant. In a typical case of 128 scan lines, the maximum frame rate is 30 frames per second.

One method used to implement real-time sector scanning is to cause one or a plurality of transducers to move so as to generate a sector scan pattern. This approach is called "mechanical sector scanning". An alternative method which has found some application uses a transducer array with electronic steering of the beam.

A common method used to achieve a sector scan mechanically is to mount a number of transducers on the side of a barrel-shaped member which is mounted in a housing having an acoustic window. When the barrel-shaped member is rotated about its axis, each transducer in turn is presented to the window and is activated while it rotates before the window. Thus, each transducer generates a sector scan of ultrasonic echo lines of sight. As the active transducer passes away from the window, the next transducer enters the window area and becomes active. This method, known as the "spinner" technique, has the advantage that, because it involves continuous rotation of a balanced member, vibration is not a problem. Also, the angular speed is constant, allowing a constant angular line spacing and the largest possible frame rate.

Another method which has been used to achieve a sector scan mechanically is to use a single transducer which is mounted to oscillate about an axis which passes through the transducer. The mounting is driven by a crank to produce an angular oscillatory motion of the transducer. Such an oscillating transducer is known as a "wobbler". As this is the starting point for the improvement in real-time scanning which is achieved with the present invention, it will be discussed in some detail.

To avoid high angular accelerations, the oscillatory motion of the "wobbler" transducer is faster in the centre of the scan and slower towards the edges, where the scan direction reverses. As the pulse repetition rate of the ultrasound transmit pulses is constant with time, the spacing of scan lines in the image generated using this type of equipment is greatest at the centre of the scan, where the angular speed is greatest, and is least near the edges of the scan as the angular speed is reduced. As the scan rate is set by the maximum angular distance between scan lines, the angular speed at the middle of an oscillatory scan is the same as that of the constant angular speed of a spinner scanner. Since the lines of sight of the ultrasonic pulses in other parts of the scan are more crowded, and the scan time is proportional to the number of lines, the presence of the extra lines means that more time is required for a scan. In fact, the total scan time is greater by about a factor of two when compared with the spinner technique. This consideration leads to a maximum frame rate for an oscillatory scan being about half that for a constant angular speed spinner scan.

This oscillatory or "wobbler" approach has benefits in that the equipment used can be made lighter, and a smaller coupling area to the body is required. For these reasons, it has been advantageous to employ this approach in many areas of clinical examination.

There is another advantage of the "wobbler" approach which is related to the method commonly used to interpolate the image content between the ultrasound data lines. The most economical interpolation method is to interpolate linearly along horizontal lines in the image, as this can be done during the display of the individual scan lines. The properties of the ultrasonic image are such that the most appropriate way to interpolate is at right angles to the scan line, as described more fully in a paper by D E Robinson and P C Knight entitled "Interpolation Scan Conversion in pulse-Echo Ultrasound", which was published in *Ultrasonic Imaging*, Volume 4, pages 297-310, 1982. For parts of the image near the centre of the scan, the sector scan lines are at right angles to the horizontal raster lines and the interpolation is appropriate. Towards the edges of the scan, the ultrasound lines are inclined and horizontal interpolation becomes less appropriate, but this can be overcome by reducing the angular spacing of the data lines, which is a property of the oscillating wobbler mechanical scan.

With the improvement in image quality available in real-time scanners, the older compound scan technique fell out of favour. However, there are a number of specific advantages in the compound scan technique which make a combination of real-time scanning and compound scanning attractive. These advantages arise from the need to carry out specific functions which are additional to the imaging. One of these specific functions is the measurement of fluid flow in vessels using the observed Doppler shift of echo signals in conjunction with the determination of the cross-sectional area of the vessel and angle between the axis of the vessel and the incident beam of ultrasonic energy. An example of the use of the Doppler effect was described by G Kossoff in the specification of Australian Pat. No. 492,512, which corresponds to U.S. Pat. No 3,939,707, U.K. Pat. No. 1,459,849 and Japanese patent application No. 54311/74. The use of at least two transducer positions is needed for the determination of sound speed within examined tissue, as was shown by D E Robinson in the specification of Australian Pat. No. 523,895 (which corresponds to U.S. Pat. No. 4,252,025), and by D E Robinson, C F Chen and L S Wilson in their paper entitled "Measurement of Velocity of Propagation from Ultrasonic Pulse-Echo Data", which was published in Ultrasound in Medicine and Biology, volume 8, No. 4, pages 413-420, 1982.

It is an obvious progression from these examples of the prior art to attach two real-time mechanical sector scanners to an arm and provide appropriate display means to combine the spatially related images from the two transducer positions, which is well known from compound scanning. In this straight-forward application of two "wobbler" real-time sector scanners, the maximum frame rate for a full sector scan from each transducer would be just half that for each sector alone. However, this is undesirable as it gives rise to an annoying flicker in the image and blurring and jerkiness of the images of moving structures.

DISCLOSURE OF THE INVENTION

An object of the present invention is the provision of a method and apparatus for combining two concurrent sector images derived by the oscillating transducer method so that the frame rate is identical with that of a single sector scan from one of the transducers.

This objective is achieved by (a) running the two "wobbler" transducers synchronously, but out of phase with each other, so that when one of the transducers is generating beams of ultrasonic energy at its point of maximum angular velocity, the other "wobbler" transducer is generating signals while its angular velocity is substantially zero (that is, when changing the direction of scan), and (b) instead of supplying activating signals to one transducer for a complete scan of its ultrasound beam, then doing the same for the other transducer (or supplying the activating signals to each transducer separately), some of the activation signals are "stolen" from the transducer having substantially zero angular velocity and are supplied to the rapidly scanning transducer. When each transducer is substantially mid-way between the region of maximum angular velocity and the region of zero angular velocity, the signals to activate the transducers are fed to the two transducers alternately. With this arrangement, and a steady transition from one state of supply of activating pulses to the other state of supply of such pulses, two very adequate sectional images are obtained in half the time that one normal double sector scan is obtained for a compound scan echogram.

Thus according to the present invention, there is provided a method of producing a sectional ultrasonic echogram of an object comprising the steps of (a) mounting a pair of ultrasonic transducers in spaced-apart relationship, each transducer being adjacent to said object and each transducer being adapted to transmit pulses of ultrasonic energy into the object when the transducer is activated and to receive echoes of the pulses from acoustic discontinuities in the object;

(b) oscillating each said transducer about a respective axis which passes through the transducer, each transducer being oscillated through substantially the same predetermined angle with the same period of oscillation;

(c) synchronising the oscillation of the transducers so that when one of the transducers is at substantially the mid-point of its predetermined angle of oscillation, the other transducer is in the region of one of the edges of its predetermined angle of oscillation;

(d) providing a stream of electrical pulses at a constant pulse repetition rate, each of said electrical pulses being adapted to activate the ultrasonic transducers; and (e) supplying the electrical pulses to the ultrasonic transducers in such a manner that (i) when one of the transducers is in the region of said mid-point of its predetermined angle of oscillation, it receives a predominance of the electrical pulses, and (ii) when the transducers are each between their respective mid-points of their angles of oscillation and an edge of their angles of oscillation, the electrical pulses are supplied alternately to the transducers.

Also according to the present invention, there is provided a transducer assembly for ultrasonic scanning equipment, said assembly comprising (a) a pair of mechanically oscillatable ultrasonic transducers mounted in spaced apart relationship, each said transducer being adapted to transmit pulses of ultrasonic energy along a beam into an object when activated and to receive echoes of such pulses of ultrasonic energy from acoustic discontinuities in the path of the beam, each transducer being adapted to oscillate through substantially the same predetermined angle to vary the direction of transmission of said beam through the same angle;

(b) means to oscillate said transducers with the same period of oscillation and with the oscillation of the transducers synchronised so that when one of the transducers is at substantially the mid-region of its predetermined angle of oscillation, the other transducer is in the region of one of the edges of its predetermined angle of oscillation;

(c) means to generate a stream of electrical pulses at a constant pulse repetition frequency, each of said electrical pulses being adapted to activate the transducers; and (d) means to supply the pulses of said stream to the transducers in such manner that the electrical pulses are predominantly supplied to a transducer when it is in the region of said mid-region of its angle of oscillation, and the electrical pulses are supplied substantially alternately to the transducers when the transducers are each between the mid-regions of their angles of oscillation and an edge of their angles of oscillation.

These features of the present invention will be illustrated in the following description of an embodiment of the present invention. In the following description, reference will be made to the accompanying drawings.

DETAILED DESCRIPTION OF THE ILLUSTRATED EMBODIMENT

Figure 1:
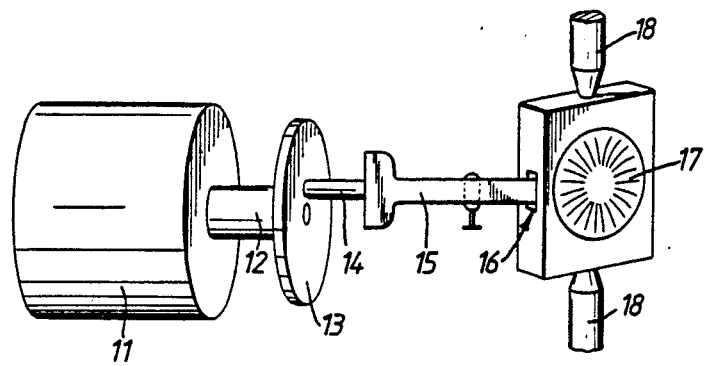
FIG. 1 is a diagram of one example of a prior art mechanical drive which produces the oscillatory motion of a "wobbler" transducer.
Figure 2:
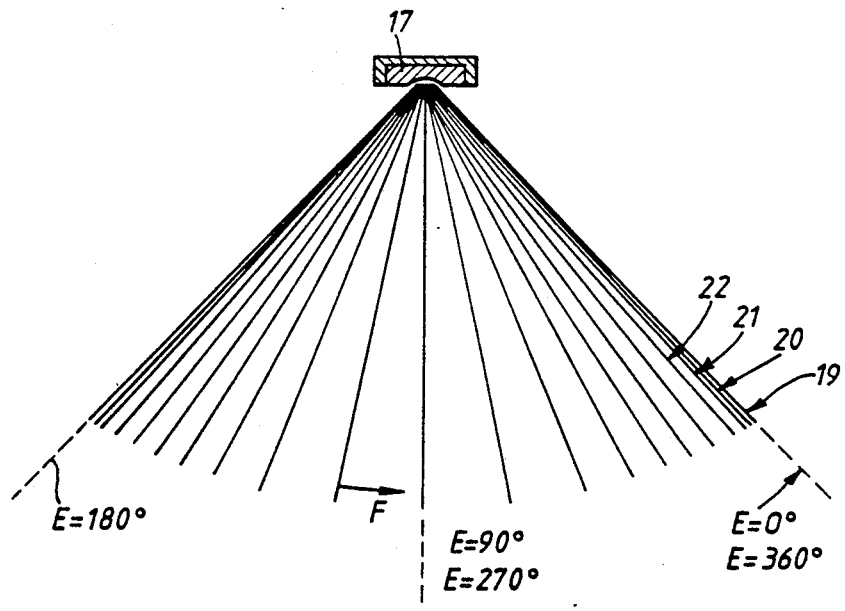
FIG. 2 is a representation of the spacing of ultrasound scan lines obtained at a constant pulse repetition frequency using the "wobbler" system illustrated in FIG. 1.

In the known form of "wobbler" scanner mechanism illustrated in FIG. 1, a motor 11 turns a shaft 12 and a plate 13 (which is connected rigidly to shaft 12) at constant angular speed. The plate 13 has a pin 14 which engages in a hole in a yoke 15. The yoke 15 is connected by pivots 16 to one side of an ultrasonic transducer 17. The transducer 17 is supported by pivots 18 for oscillation about an axis provided by the points of the pivots 18. This mechanism produces an oscillatory motion of the transducer 17. As shown in FIG. 2, the line of sight of pulses of ultrasonic energy generated by the transducer will vary with time in a non-linear way. In fact, the angle F of its line of sight away from the direction of the axis of the system is given by the relationship:

$$F = \arctan K \cdot \cos E$$

where E is the angle turned by the motor shaft 12 and K is a constant depending on the linkage dimensions. For a maximum total scan angle of 90°, the value of K is unity.

In the scan pattern shown diagrammatically in FIG. 2, the lines of sight 19, 20, 21, 22, .... are generated at equal increments of the angle of the motor shaft 12, by the transducer 17.

As can be seen from FIG. 2 (or interpreted from the equation for F above), the lines of sight are spread out at the centre of the scan and are crowded towards the edges. In practice, the maximum motor shaft rotation speed is set by the maximum pulse rate for the penetration depth required for the pulses of ultrasonic energy generated by the transducer 17, and by the maximum angle increment in the scan pattern.

The basis for the present invention is the appreciation that if two "wobbler" transducers, as illustrated in FIG. 1, are used simultaneously to obtain a compound scan of an object, when one of the transducers is in a position where the actual scan angle increment is less than the maximum allowable, some scan lines can be "stolen" from the scan of one "wobbler" and used in the scan of the other "wobbler". Thus the total time for a complete scan from each "wobbler" can be reduced. To achieve this time saving, it is necessary to control the timing of the two scans to that as one "wobbler" transducer is passing through the middle of its scan pattern and requires all its lines, the other transducer is at one end of its angular scan, where the lines are all crowded together and many lines can be omitted without exceeding the maximum allowable angle increment between lines of sight.

Figure 3:
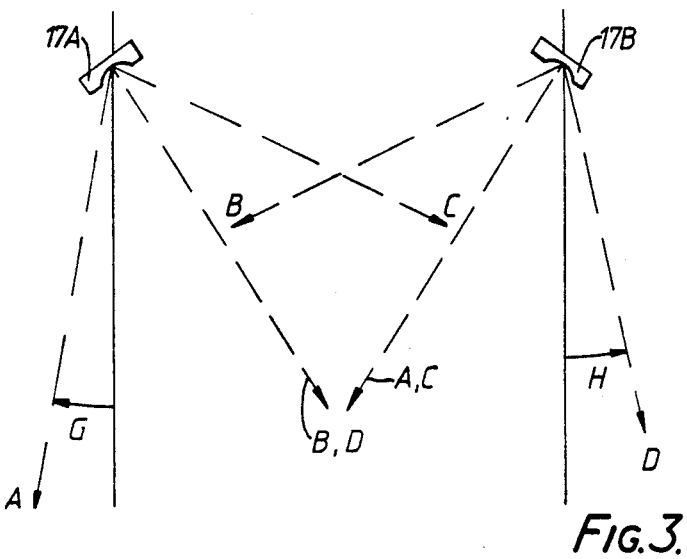
FIG. 3 is a diagram of the overlapping compound scan pattern from a pair of oscillating transducers, assembled in accordance with the present invention, showing the required timing between the two scans.

Such a "double wobbler" system is illustrated in FIG. 3. In this diagram, two transducers 17A and 17B are located at positions 32, 33, and the lines of sight of the beams of ultrasonic energy which are generated at the centre and at the two edges of each sector scan are shown. The letters A, B, C, D represent simultaneously occurring ultrasound beam directions from the two transducers. As can be seen from the diagram, while one transducer has beam line A at the edge of the the scan, the other has beam line A at the centre, and so on. The angle for each sector, G and H, is measured from the vertical lines drawn in FIG. 3.

Figure 4:
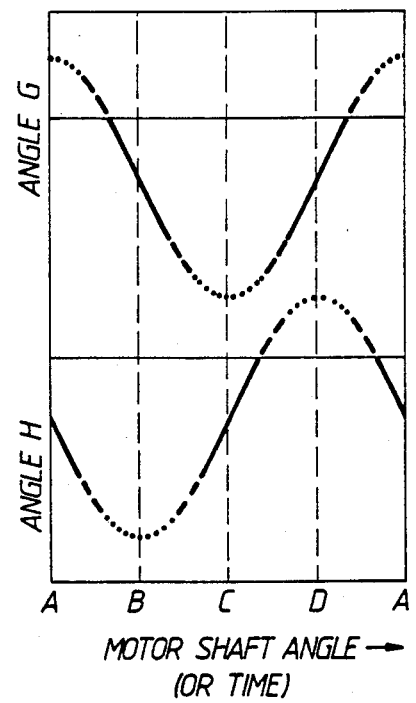
FIG. 4 is a plot of the scan angle of each "wobbler" transducer as a function of time, or of motor shaft angle.

The relationship between the two scans is further illustrated in FIG. 4, in which the angles G and H are plotted as a function of the motor shaft angle, or time.

The line stealing process is not necessarily carried out symmetrically. For instance, if the display system associated with the compound scanner which uses the "double wobbler" arrangement of the present invention uses TV horizontal line interpolation, the maximum desirable angle increment is less for lines near B for transducer 17B (and near C for the transducer), and is greater for lines near D for transducer 17B (and near A for transducer 17A).

One implementation of this process is shown in FIG. 4. In parts of the scan where the curve has a solid line, that transducer is active and using most or all of the available activation or transmit electrical pulses. In parts of the curve where the curve is accompanied by a dashed line, the transducers are sharing the electrical pulses approximately equally. Where the curve is a dotted line, the transducer is receiving only occasional lines and the other transducer is predominantly active.

It should be noted that at the end of the scan, only one scan direction is needed to obtain the information. For instance, for motor angle B and beam angle H, the information may be obtained from either immediately to the left or right of the line showing angle B since the two would be taken very close together in time and thus be similar images. The choice as to which lines are "stolen" depends on the relative demand for lines from the other transducer at that time.

To implement the present invention, a programmed microprocessor and standard digital electronic techniques may be used. One circuit arrangement that has been used successfully by the present inventor is illustrated in FIG. 5.

Figure 5:
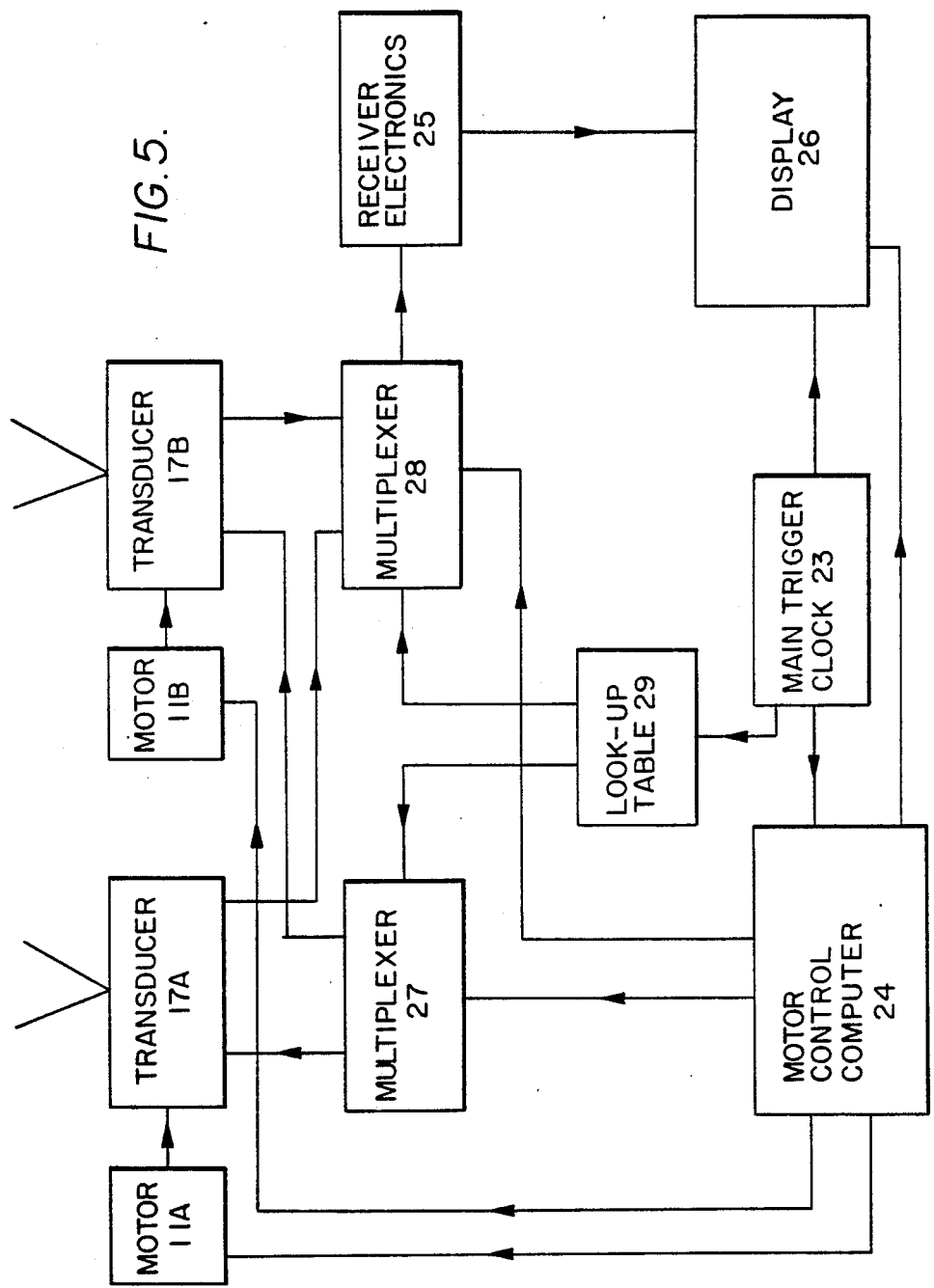
FIG. 5. Is a block diagram of an electronic circuit which may be used to implement the present invention.

In the circuit arrangement depicted by FIG. 5, a main trigger clock 23 is used in conjunction with a conventional single transducer ultrasound machine. The main trigger clock 23 initiates each cycle of operation of the ultrasound machine. This comprises stepping the transducer to a new position by operation of motor control computer 24 and motor 11, transmitting an ultrasonic pulse from transducer 17 and receiving echos which are processed in conventional receiver electronics 25 and displayed on display 26.

In this embodiment of the invention, the motors 11 associated with the "wobbler" transducers are stepper motors operating at either 200 steps per revolution, or 400 steps per revolution. The microprocessor is used to control the synchronization of the driving shafts 12 of each stepper motor, and steps them in response to pulses from system trigger clock 23. The additional components required to implement the invention are the transmit multiplexer 27, the receive multiplexer 28 and the look-up table 29. The multiplexers 27 and 28 are conventional units which serve to switch the ultrasound system from one transducer to the other. The motor control computer 24 outputs a line number corresponding to the current motor shaft angle to the look-up table 29 which controls the operation of the multiplexers 27, 28 by outputting either a 1 or a 0 to each multiplexer to activate either of transducer 17A or 17B for each motor step according to the relationship of FIG. 4.

In prototype equipment constructed to test the present invention, "look-up" tables of 400 lines and of 800 lines, specifying where the next electrical pulse is to be directed, have been incorporated into the microprocessor. The 400 lines look-up table was used with the stepper motors operating at 200 steps per revolution and the 800 lines look-up table was used with the stepper motor operating at 400 steps per revolution. The equipment functioned properly whichever of these tables was used to control the allocation of an activating electrical pulse to a transducer.

Those skilled in this art will recognise that although a specific embodiment of the synchronised, phased, "double wobbler" arrangement has been illustrated, variations of this embodiment may be made without departing from the present inventive concept. For example, a single motor, with appropriate drives, could be used to control the oscillation of both "wobbler" transducers.

I claim:

1. A method of producing a sectional ultrasonic echogram of an object comprising the steps of
   (a) mounting a pair of ultrasonic transducers in spaced-apart relationship adjacent to said object, each transducer transmitting pulses of ultrasonic energy into the object when the transducer is activated and receiving echoes of the pulses from acoustic discontinuities in the object;
   (b) oscillating each said transducer about a respective axis which passes through the transducer, each transducer being oscillated through substantially the same predetermined angle with the same period of oscillation;
   (c) synchronising the oscillation of the transducers so that when one of the transducers is at substantially the mid-point of its predetermined angle of oscillation, the other transducer is in the region of one of the edges of its predetermined angle of oscillation;
   (d) providing a stream of electrical pulses at a constant pulse repetition rate, each of said electrical pulses being adapted to activate the ultrasonic transducers; and
   (e) supplying the electrical pulses to the ultrasonic transducers in such a manner that
      (i) when one of the transducers is in the region of said mid-point of its predetermined angle of oscillation, it receives a predominance of the electrical pulses, and
      (ii) when the transducers are each between their respective mid-points of their angles of oscillation and an edge of their angles of oscillation, the electrical pulses are supplied alternately to the transducers.

2. A method as defined in claim 1, in which the step (e) is effected using a programmed microprocessor to direct each electrical pulse to one of said transducers in accordance with instructions included in a look-up table in said microprocessor.

3. A method as defined in claim 2, in which the synchronism of step (c) is also controlled by said microprocessor.

4. A transducer assembly for ultrasonic scanning equipment, said assembly comprising
   (a) a pair of mechanically oscillatable ultrasonic transducers mounted in spaced apart relationship for transmitting pulses of ultrasonic energy along a respective beam into an object when activated and receiving echoes of such pulses of ultrasonic energy from acoustic discontinuities in the path of the beam, each transducer oscillating through substantially the same predetermined angle to vary the direction of transmission of said respective beam through the same angle;
   (b) means for oscillating said transducers with the same period of oscillation and with the oscillation of the transducers synchronised so that when one of the transducers is at substantially the mid-region of its predetermined angle of oscillation, the other transducer is in the region of one of the edges of its predetermined angle of oscillation;
   (c) means for generating a stream of electrical pulses at a constant pulse repetition frequency, each of said electrical pulses being adapted to activate the transducers; and
   (d) means for supplying the pulses of said stream to the transducers in such manner that the electrical pulses are predominantly supplied to a transducer when it is in the region of said mid-region of its angle of oscillation, and the electrical pulses are supplied substantially alternately to the transducers when the transducers are each between the mid-regions of their angles of oscillation and an edge of their angles of oscillation.

5. An assembly as defined in claim 4, in which said means to supply the pulses of said stream includes a programmed microprocessor which apportions each electrical pulse to one of said transducers in accordance with instructions contained in a look-up table.

6. An assembly as defined in claim 5, in which said means to oscillate said transducers comprises a pair of electrical motors, each motor having a drive shaft which controls the oscillation of a respective one of said transducers, and said microprocessor also controls the synchronisation of said drive shafts.

* * * * *